United States Patent [19]

Faccioli et al.

[11] Patent Number: 5,292,322
[45] Date of Patent: Mar. 8, 1994

[54] CLAMPING COUPLING FOR AN EXTERNAL FIXATOR

[75] Inventors: Giovanni Faccioli, Monzambano; Daniele Venturini, Verona, both of Italy

[73] Assignee: Orthofix S.r.l., Bussolengo, Italy

[21] Appl. No.: 86,156

[22] Filed: Jul. 1, 1993

Related U.S. Application Data

[63] Continuation-in-part of Ser. No. 788,136, Nov. 5, 1991.

[51] Int. Cl.[5] .................................................. A61F 5/04
[52] U.S. Cl. ............................................ 606/59; 606/53
[58] Field of Search ................... 606/53, 54, 55, 57, 606/59, 60, 72, 86, 87, 88, 89; 403/141, 157, 165, 287, 289, 290

[56] References Cited

U.S. PATENT DOCUMENTS

| | | | |
|---|---|---|---|
| Re. 31,809 | 1/1985 | Danielleto et al. | 606/57 |
| 4,135,505 | 1/1979 | Day | 606/59 |
| 4,483,334 | 11/1984 | Murray | 606/54 X |
| 4,621,627 | 11/1986 | DeBastiani et al. | 606/54 X |
| 5,019,077 | 5/1991 | DeBastiani et al. | 606/59 X |

*Primary Examiner*—Danton D. DeMille
*Assistant Examiner*—Sam Rimell
*Attorney, Agent, or Firm*—Hopgood, Calimafde, Kalil, Blaustein & Judlowe

[57] ABSTRACT

A bone-screw or the like clamping coupling comprises two articulated half shells which must be bolted to each other for assembly to bone screws or the like. Articulation is via loosely pivoted interconnection of the half shells at one longitudinal end of the coupling, and one of the half shells carries ball-joint connection structure that is adapted for selectively detachable connection to an external fixator that has a coacting ball-joint connecting formation.

5 Claims, 1 Drawing Sheet

CLAMPING COUPLING FOR AN EXTERNAL FIXATOR

RELATED CASE

This application is a continuation-in-part of copending application, Ser. No. 07/788,136, filed Nov. 5, 1991.

BACKGROUND OF THE INVENTION

The invention relates to orthopedic-fixation devices and in particular to a clamping coupling for a fixator of the nature disclosed in U.S. Pat. No. 4,312,336 (now Reissue Pat. No. Re. 31,809).

Said patent disclosed an external fixator having a central body part with clamping means at each of the respective ends of the body part. Each of the clamping means is developed (1) to receive and fix in place bone screws or pins and (2) to detachably achieve a ball-joint connection to the central body part, via a bayonet lock or via a threaded lock. In this way, the bone screws are connected to the central body part of the fixator.

More specifically, with respect to the clamping means for an external fixator, clamping action is achieved by and between elongate confronting faces of two half shells, the confronting faces having corresponding transverse grooves by which one or more bone screws, pins or the like are located when the half shells are bolted to each other to secure their clamped assembly to the bone screws or the like. The longitudinal end of one of these half shells carries ball-joint connecting means that is adapted for detachable connection to a coacting ball-joint connection at either of the two longitudinal ends of an external fixator.

Although bone-screw clamps of the character indicated have been generally adopted and are satisfactory, they do involve totally separable component parts and in certain cases exhibit manipulating inconvenience in the course of assembly to and/or disassembly from bone screws.

BRIEF STATEMENT OF THE INVENTION

The object of the present invention is to improve the construction of a clamping coupling of the character indicated by providing a convenience feature which facilitates manipulation in use.

The invention achieves this object by providing a bonescrew or the like clamping coupling wherein the two half shells which must be bolted for assembly to bone screws are articulated via their loosely pivoted interconnection at one longitudinal end of the coupling. One of the half shells carries ball-joint connection structure that is adapted for selectively detachable connection to an external fixator that has a coacting ball-joint connecting formation. And the loosely pivoted interconnection of the two half shells is preferably at the opposite longitudinal end of the coupling.

The loosely pivoted connection of the two half shells provides the convenience of easier manipulation of the shells in their assembly or disassembly with respect to installed bone screws. The released and loosely pivoted shell remains continuously accessible and cannot be mislaid, as when a fixator must be periodically removed to permit bone-strength measurements in the course of a extended period of bone-fracture repair. More specifically, when removing the fixator for such a measurement, the ball-joint connections to bone-screw clamps at both longitudinal ends of the fixator must remain locked, to preserve and reestablish the fixed relation of bone screws on proximal end distal sides of the fracture which is being repaired; in that circumstance, the ready manipulability of loosely pivoted half shells at both sides of the fracture site greatly aids the speed and efficiency of reestablishing precise orientations, once the bone-strength measurements have been made.

DETAILED DESCRIPTION

A preferred embodiment of the invention will be described in detail, in conjunction with the accompanying drawings, in which.

Figure 1:
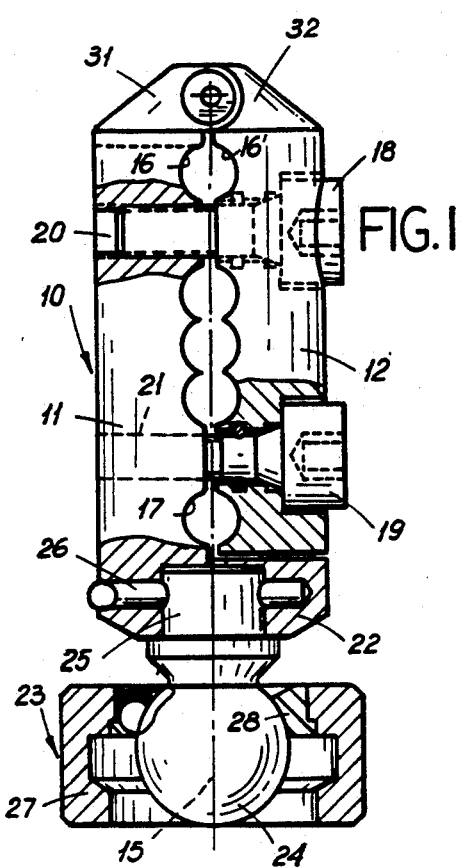
FIG. 1 is a view in side elevation of a bone-screw clamp of the invention, partly broken-away and in longitudinal section.
Figure 2:
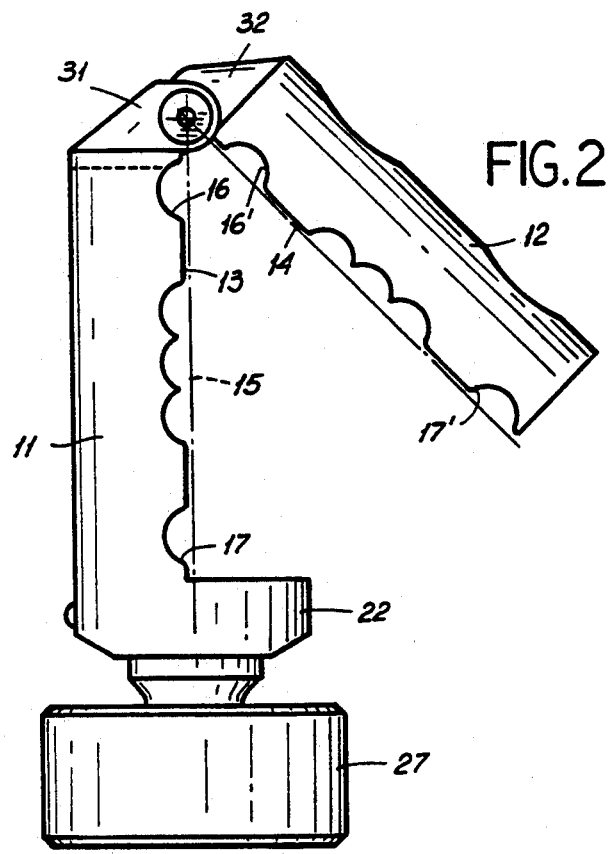
FIG. 2 is another view in side elevation, with pivoted components in opened relation.

Referring initially to FIGS. 1 and 2, a clamping coupling of the invention is seen to comprise a body 10 defined by two elongate half shells, shown as semicylindrical members 11, 12 having confronting clamp faces 13, 14 in essentially a single plane which includes the central axis 15 of the coupling. Matching opposing pairs of grooves 16, 16', 17, 17' etc. in the confronting faces 13, 14 are sized for bone-screw, pin or drill-guide reception and location, when the half shells 11, 12 are bolted for clamping action. To this end, bolts 18, 19, countersunk in longitudinally spaced bores through half shell 12, engage tapped bores 20, 21 in half shell 11.

Half shell 11 is the primary body part of the clamp 10. At its proximal end of detachable connection to one of the two longitudinal ends of an external fixator, as of the kind shown in said Reissue Pat. Re. 31,809, the half shell 11 is integrally formed with a base 22 that is preferably symmetrical about the central axis 15; and ball-joint connecting means 23 carried by base 22 is adapted for selectively detachable connection to the external fixator via a coacting ball-joint connecting formation of the fixator (not shown). Specifically, the ball-joint connecting means 23 of coupling 10 is seen to comprise a ball 24 having an integral stem 25 that is seated and fixed in an axial end bore of base 22, being retained by a transverse pin 26. A collar 27 establishes at 28 one half of the necessary concave seating required for universal ball-joint action, but the ball joint and its action are not realized until after releasable assembly of connecting means 23 to a ball-joint connecting formation which characterizes either of the longitudinal ends of a coacting fixator, it being understood that such a connecting formation includes the other half of necessary concave seating required for ball-joint action, as well as means (also not shown) for selectively releasably connecting to the fixator and for clamping the ball-joint connection in a desired angular relation of the clamp axis 15 to the central axis of the fixator.

In said reissue patent, a bone-screw clamp is selectively detachable via ball-joint connection to one of the longitudinal ends of an external fixator, and the clamp is generally as described above, wherein the half shells 11, 12 are separate parts which become totally separate upon thread disengagement of the clamp bolts 18, 19. Such total separability of clamp parts has its handicapping disadvantages, an illustrative one of which has been noted above. The invention overcomes such disadvantages by providing a loosely pivoted or hinged connection of the half shells 11, 12, this loosely pivoted connection being at the distal end of the half shells, as shown.

Specifically, the preferred hinge action is provided by a pinned clevis connection involving a transverse pin 30 carried by spaced forked projections 31 at the distal end of one of the half shells (11), with pin 30 engaging a single such projection 32 at the distal end of the other half shell (12). The single hinge projection 32 preferably is of width to derive slidable but stabilizing support from adjacent sidewalls of the forked projections 31; and, also preferably, the bore in projection 32 for passage of the pivot pin 30 is oversized, to the extent of providing a measure of radial play in the articulation of half shell 12 with respect to the half shell 11.

Figure 3:
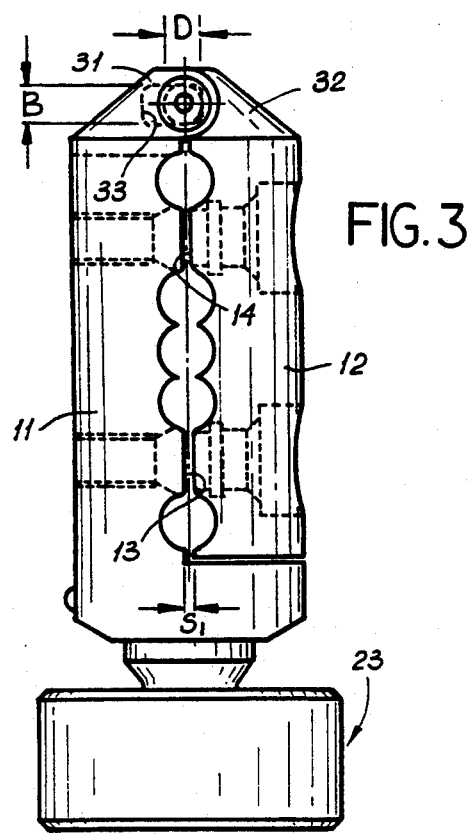
FIG. 3 is a view similar to FIG. 1, in aid of discussing a predetermined play in the pivotal connection of clamp parts.
Figure 4:
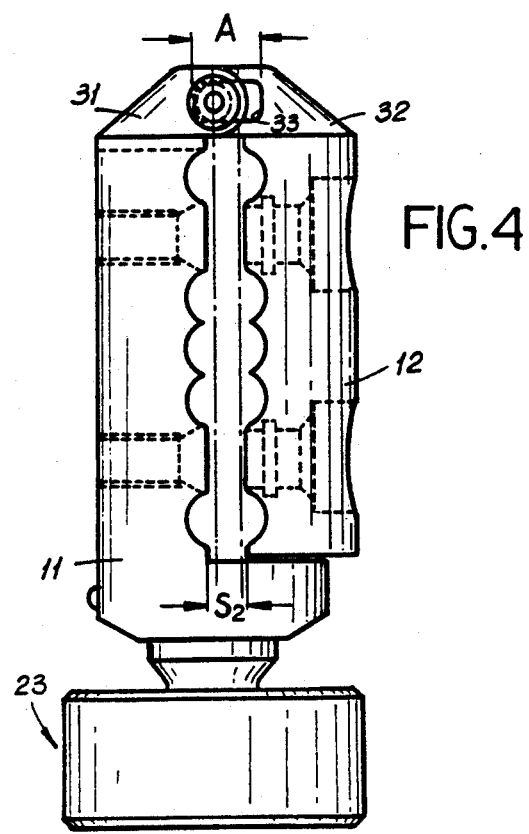
FIG. 4 is a view similar to FIG. 3, to show the range of play in the pivotally connected parts.

In FIGS. 3 and 4, the oversize opening is identified 33 and is seen to be generally rectangular, with a major-axis dimension A that is transverse to the generally radial plane of the confronting clamp faces 13, 14 and that is substantially twice the operative diameter D of pin 30. The opening 33 has a minor-axis dimension B that exceeds the operative pin diameter D so as to allow at least some relative axial displaceability of half shells 11, 12 with respect to each other, for utmost fidelity in their engagement to bone screws or the like at the groove pairs (16, 16'; 17, 17') involved in a particular use of the clamping coupling. FIGS. 3 and 4 demonstrate the range of half-shell clamped spacing available for clamped retention of a range of bone-screw or the like sizes, by reason of the indicated loosely pivoted relation, namely, from a minimum parallel spacing $S_1$ of the confronting faces 13, 14 in FIG. 3, to a maximum parallel spacing $S_2$ thereof in FIG. 4.

What is claimed is:

1. As an article of manufacture, an elongate clamping coupling having at one end ball-joint connection means adapted for selectively detachable connection to an external fixator having a coacting ball-joint connecting formation, said clamping coupling comprising two elongate half shells having confronting separable portions that are grooved for reception of bone screws or bone pins, clamp bolts for clamping said shells together for fixed retention of bone screws or the like in said grooves, said ball-joint connection means being connected to said one end of one of said half shells, and a pinned hinge connection of said half shells to each other at the other end of said half shells.

2. The article of claim 1, in which said hinge connection is a pinned clevis connection between spaced forked projections at said end of one of the half shells, and a single projection between said forked projections and at said end of the other of said half shells.

3. The article of claim 2, in which said confronting separable portions are in a generally longitudinal plane which includes said pinned connection.

4. The article of claim 2, in which the single projection of said other half shell has an opening for said pinned connection, wherein the opening is oversize to the extent of establishing a measure of radial play in the articulation of said half shells via said pinned connection.

5. The article of claim 3, in which the single projection of said other half shell has a generally oval opening for said pinned connection, wherein the generally oval opening has a major axis that is generally perpendicular to said generally longitudinal plane when said half shells are in confronting relation.

* * * * *